United States Patent [19]

Gram

[11] 4,063,453

[45] Dec. 20, 1977

[54] ADJUSTABLE SPACE FRAME FOR TESTING MACHINE

[75] Inventor: Martin M. Gram, Minneapolis, Minn.

[73] Assignee: MTS Systems Corporation, Eden Prairie, Minn.

[21] Appl. No.: 773,960

[22] Filed: Mar. 3, 1977

[51] Int. Cl.² .............................................. G01N 3/10
[52] U.S. Cl. ..................................... 73/103; 100/214
[58] Field of Search .................. 73/92, 93, 94, 95, 97, 73/103; 100/214

[56] References Cited

U.S. PATENT DOCUMENTS

| | | | |
|---|---|---|---|
| 3,249,041 | 5/1966 | Johnson | 100/214 |
| 3,465,669 | 9/1969 | Doudet | 100/214 |

Primary Examiner—Jerry W. Myracle
Attorney, Agent, or Firm—Dugger, Johnson & Westman

[57] ABSTRACT

A load frame used for testing purposes which includes means for reacting side loads between upper and lower cross heads of platens of a press or load frame.

12 Claims, 6 Drawing Figures

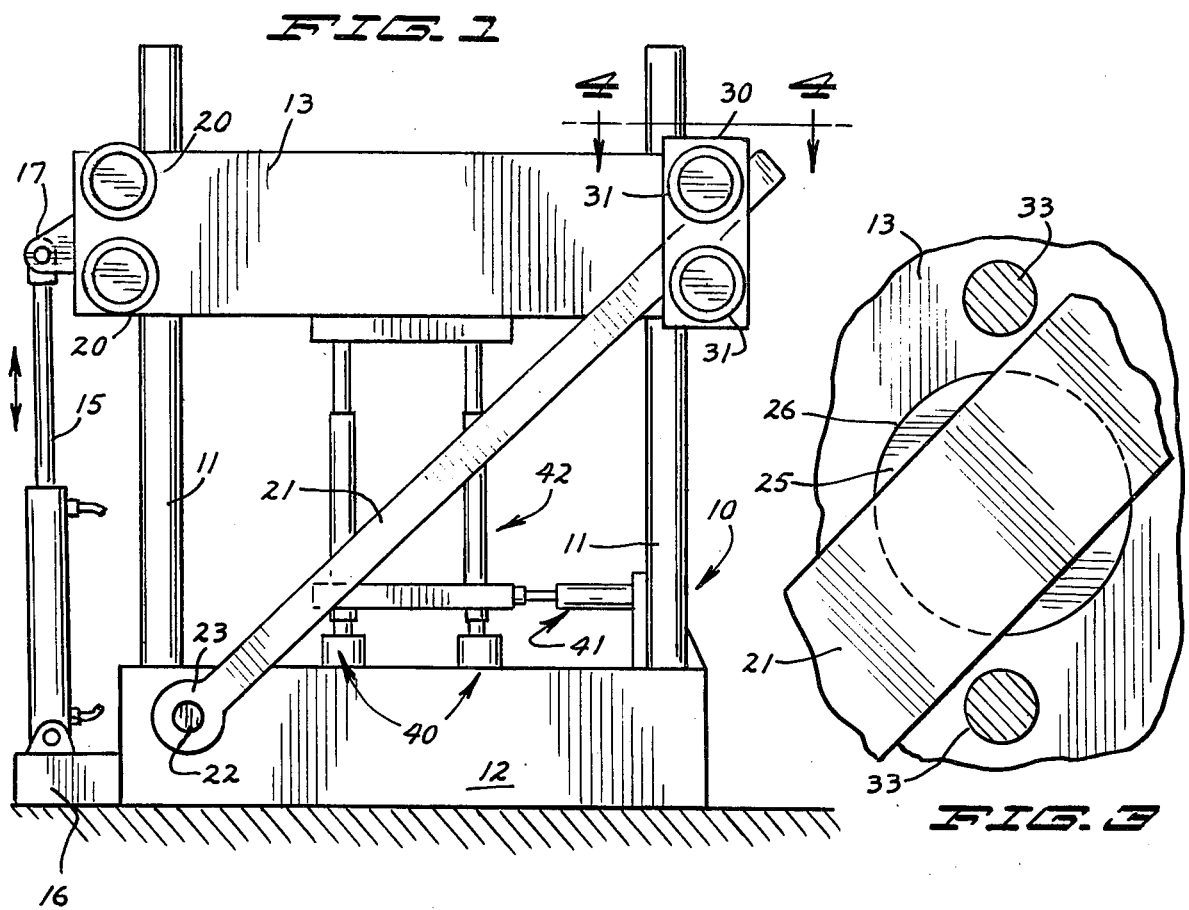
FIG. 1
FIG. 3
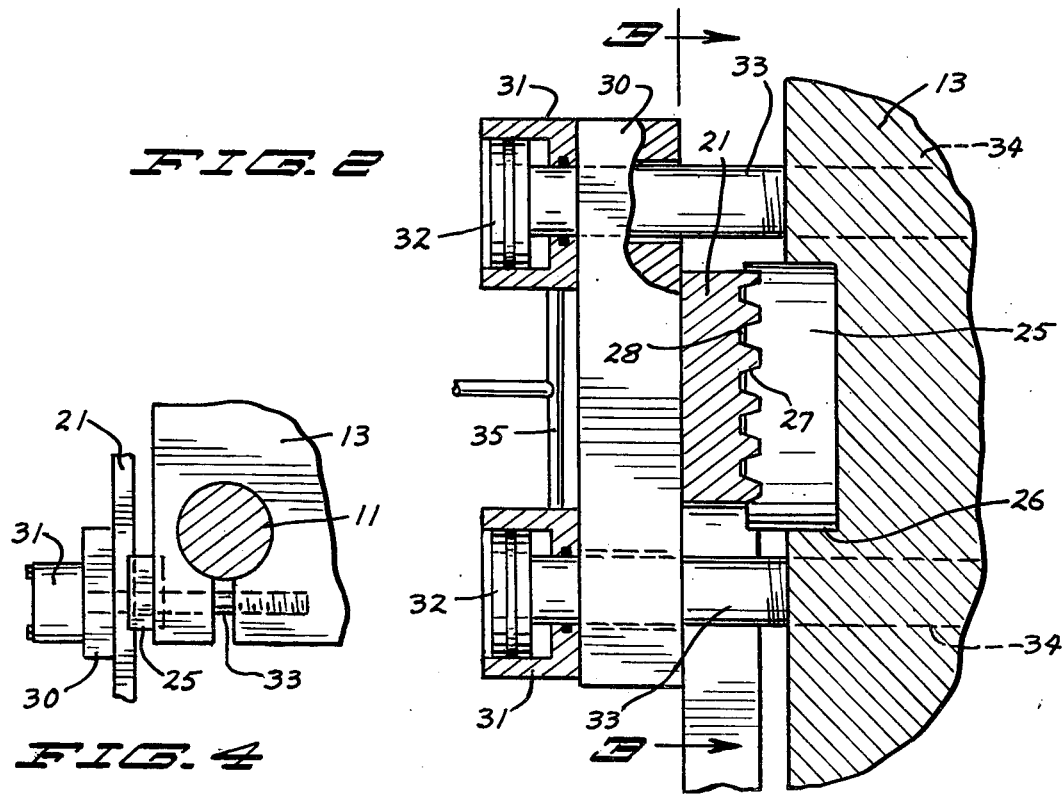
FIG. 2
FIG. 4

4,063,453

ADJUSTABLE SPACE FRAME FOR TESTING MACHINE

BACKGROUND OF THE INVENTION

1. FIELD OF THE INVENTION

The present invention relates to load frames and in more particularly to means for reacting side loads between the upper and lower cross heads or platens of a load frame.

2. PRIOR ART

In the prior art, the assignee of the present invention, MTS Systems Corporation of Eden Prairie, Minnesota has been engaged in making and selling various multiple column load frames for various uses.

For example, the corporation is the owner of U.S. Pat. No. 3,442,120 which shows a resonant hydraulic fatigue testing device utilizing a load frame with upright columns, wherein suitable hydraulic clamps can be used on the smooth columns (or other types of clamps if desired). Such clamps are conventionally used and have been used for many years.

Heavy load frames having four columns, one on each of the corners of a square or rectilinear base, and having a movable cross head mounted on the columns have also been widely used.

The columns used between the platens adequately carry the vertical loads (parallel to the axes of the columns), and are capable of reacting side loads caused by specimen misalignment. Typical side load capability for load frames is less than ten percent of the axial load. Stress and deflection of the columns in horizontal direction (assuming that the columns are vertical) can thus be a problem when testing specimens that require substantial biaxial loading.

SUMMARY OF THE INVENTION

The present invention relates to a load frame comprising a support member or base platen with columns fixed to the base and extending from said base in a first direction. A second cross head or platen is mounted on the columns and is capable of having its spacing adjusted relative to the base, and wherein the assembly includes a diagonally extending brace or strut member extending from adjacent one edge of one of the platens, and diagonally upward to a position adjacent an opposite edge of the same side of the platens. The brace is capable of being clamped relative to the other platen. The diagonal brace thus is oriented to carry loads perpendicular to the axis of the support columns.

These braces or struts will be positioned to the exterior of the platens, and can be detachably secured on at least one end to permit moving them out of the way for putting specimens into the load frame if desired. The clamps that are utilized with the braces permit adjusting the platens relative to each other, as well as adequate clamping. Different types of braces can be used, and various mounting pin configurations and clamp devices can be utilized.

BRIEF DESCRIPTION OF THE DRAWINGS

FIG. 1 is a schematic representation of a load frame having a diagonal brace made according to the present invention installed thereon;

FIG. 2 is a sectional view taken generally along line 2—1 in FIG. 1;

FIG. 3 is a sectional view taken as on line 3—3 in FIG. 2;

FIG. 4 is a sectional view taken as on line 4—4 in FIG. 1;

DESCRIPTION OF THE PREFERRED EMBODIMENTS

Figure 5:
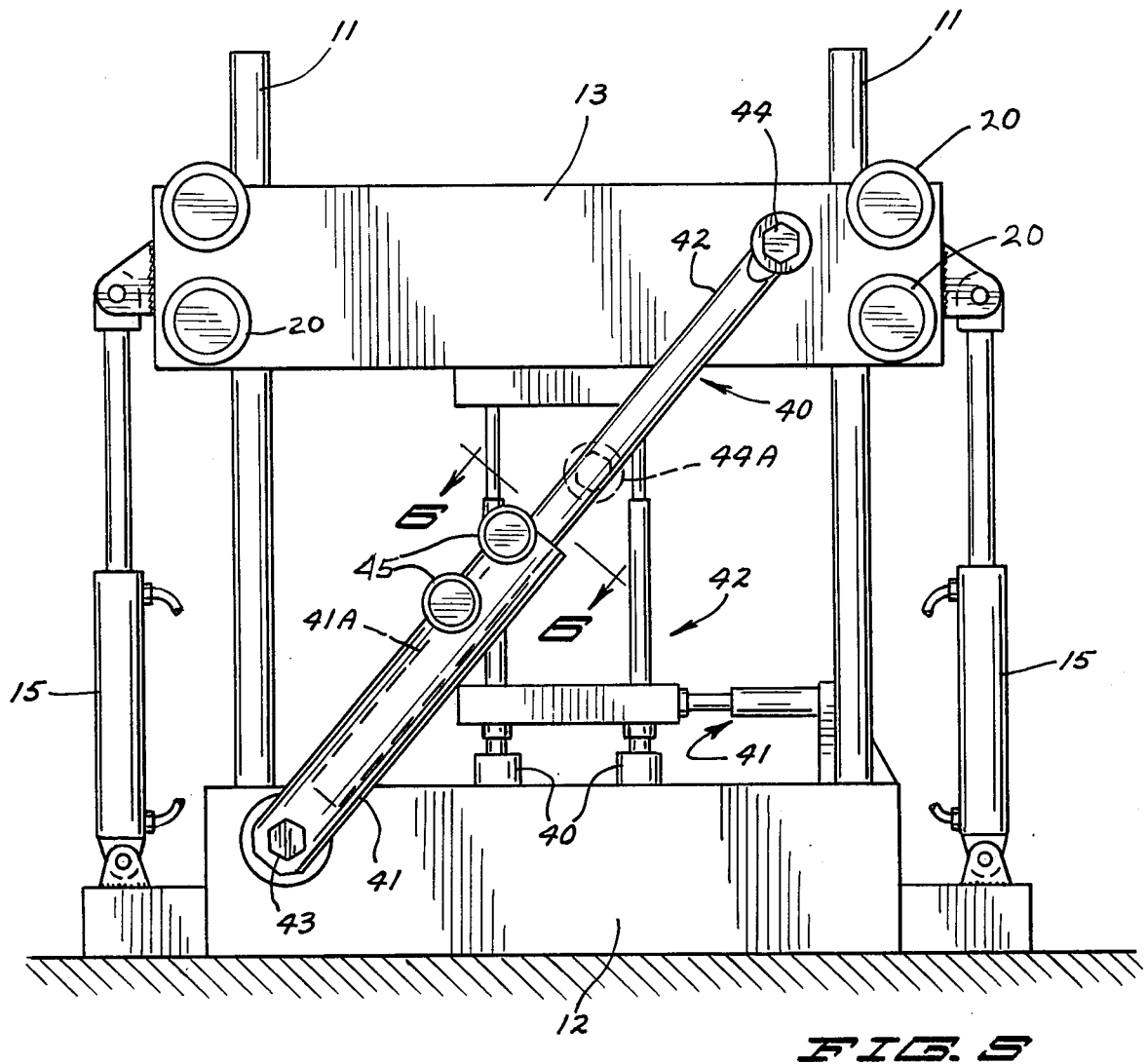
FIG. 5 is a side elevational schematic representation of a load frame substantially identical to that shown in FIG. 1 with a modified diagonal brace made according to the present invention installed thereon.

In FIG. 1 a typical load frame illustrated generally at 10 is shown in a side elevational view only, and is shown only schematically. The load frame that is shown is square when viewed in plan or top view, and has four columns on at each corner of the square frame. Two of the columns indicated at 11,11 are mounted to a base platen 12, and a cross head or platen 13 is slidably mounted on these columns. Again, it should be remembered that the columns 11,11 are spaced in square configuration and are shown only schematically for purposes of illustration in this showing.

The platen 13 is movably mounted on the columns 11,11 and can be slid along the columns and then clamped into position at a location spaced from the base platen 12. This is common in load frames, and the means of clamping onto the columns 11,11 is also well known. For schematic illustrative purposes only, the adjustment of the upper platen 13 can be accomplished through the use of a long hydraulic cylinder assembly illustrated generally at 15 that is attached to a support 16 on the base platen 12, and is also attached to a support 17 on the movable platen 13. The cylinder 15 is shown only in one corner of the load frame, but there would be a separate cylinder mounted at each of the corners for raising and lowering the upper platen 13. Other ways of raising and lowering the platen can be employed, if desired.

The upper platen 13 may be clamped onto the individual columns 11 through the use of clamping cylinders indicated generally at 20 in the corner on the left hand side, and these clamping cylinders are conventionally used in load frames made by MTS Systems Corporation, Eden Prairie, Minn. The cylinders and clamping action is generally shown in FIG. 4 in connection with the clamping of the diagonal brace of the present invention, and on the corners where the braces are not used individual clamping cylinders 20,20 are used, as shown.

The ability to react biaxial loads, that is loads which have components along and perpendicular to the columns 11 is greatly increased through the use of a diagonal brace indicated generally at 21. As shown, there is a brace on the near side of the load frame, and there would be an identical brace on the opposite side of the frame which can extend in the same direction as that shown by the brace 21.

Figure 6:
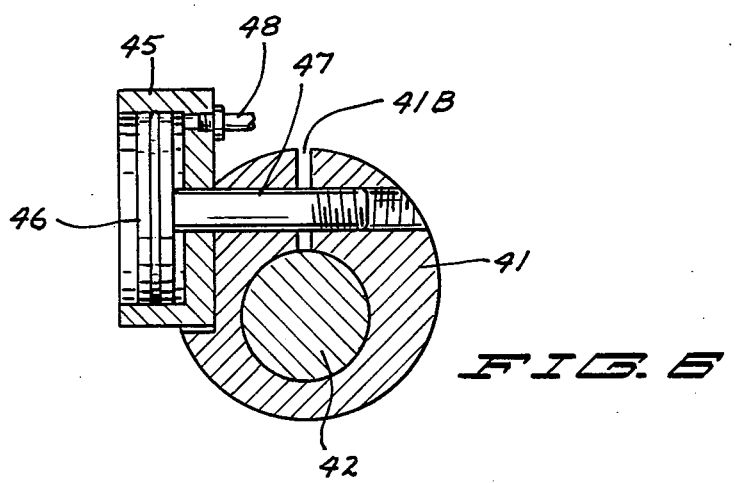
FIG. 6 is a sectional view taken as on line 6—6 in FIG. 5.

The brace 21 in the form shown is a flat bar, although the brace can be a round rod if desired, and as shown in FIGS. 5 and 6. One end of the brace 21 is pivotally mounted onto a suitable pin 22 that is fixed to the base 12. In the first form shown, a pivot pin is illustrated, but it also could be a clamp connection. For example, the hub indicated at 23 could be split and clamped with a suitable hydraulic cylinder so that once the upper platen 13 was fixed in position, and the diagonal brace 21 was also fixed at its upper end, as will be explained, the hub 23 could be clamped to the pin 22 to prevent any backlash or movement. Further, pin 22 is illustrated in the drawings as carrying loads along a single shear plane, but a support for the pin on the outside or near side of the hub 23 also can be provided to carry the load on the pin along two shear planes.

The brace 21 extends diagonally as shown toward an upper corner 24 of the platen 13. As can be seen in FIGS. 2, 3 and 4 the brace 21 engages a pivotally or rotatably mounted disc member 25 that is recessed into a suitable round recess 26 on one side of the platen 13. The disc will pivot or rotate in this recess. The brace 21 also as shown is provided with splines or teeth 27 that engage mating splines 28 in the disc 25. The two sets of splines slide relative to each other when the position of the two platens 12 and 13 is varied. The function of the spline teeth is to increase the friction coefficient of this joint (the increase is inversely proportional to the sine of the pressure angle). Various other techniques may be used to increase the friction coefficient or efficiency of this clamp joint.

The edge portion of platen 13 as shown in FIG. 4 may be split to fit around the column 11. The brace 21 is to the exterior of the platen 13. In order to clamp the platen 13 to the column 11 (as is conventionally done) and also to tightly clamp the diagonal brace 21, a clamp block 30 is mounted on the exterior of the brace 21. The clamp block 30 carries suitable hydraulic clamping cylinders 31, which may be constructed substantially identically to those shown at 20,20. The cylinders 31 have an internal piston indicated at 32 in FIG. 2. The pistons in turn are carried on pistion rods 33 that may be suitably threaded into or attached to platen 13, as indicated at 34 in dotted lines.

Hydraulic fluid pressure can be supplied to suitable conduits 35 that lead to the rod sides of the pistons 32, and when pressure is supplied through the conduits 35 the block 30 will be urged toward the platen 13. The hydraulic cylinders will clamp the diagonal brace 21 against the disc 25, and likewise then will clamp the disc 25 against the surfaces of the platen to tightly frictionally hold the brace 21 clamped in position and also hold the platen clamped on column 11. If the hub 23 also has a clamp on pin 22, it would then be clamped once the platens are positioned, so that no backlash or looseness is permitted and any side loads that would tend to bend the columns 11, would be reacted back through the diagonal brace 21 as well as through the columns 11. There would then be little or no bending of the columns.

As stated previously, if it is desired to place a test device in the space between the platens 12 and 13, and the brace 21 is in the way (there likely will be braces or struts on all four sides of the frame) the pin 22 can be removed, or the hub 23 could be released in a desired manner, and the lower end of brace 21 lifted upwardly. The disc 25 would pivot as the hub end 23 was lifted, with the upper clamp cylinders released. A winch or block and tackle can be used to lift the brace 21.

It should be noted that the platens 12 and 13 are fixed in position on the columns 11, and loading would be done through suitable load cylinders indicated schematically at 40 and 41. These cylinders can be arranged in any desired location over the platen 12 to carry out the test that is desired. In particular, the type of load frame utilized can be one where, for example mine roof supports shown schematically at 42 were being tested, and the structure forming the roof supports would be placed between the platens 12 and 13 and tested. The supports could be loaded up vertically using cylinders 40 and horizontally using cylinders 41 in order to simulate both vertical and horizontal slippage in the mine roof. The showing is schematic for purposes of illustration.

Use of the cylinders 31 for clamping both the upper end of the diagonal strut or brace and clamping that particular corner of the platen 13 to the columns 11 minimizes the additional cost and yet provides adequate clamping for both the platen and the strut itself. In this case, horizontal capacity is a ratio of vertical capacity determined by friction coefficients of the joints. Alternatively, use of a pin at each end of the diagonal strut with an independent clamp device built into the strut that allows adjustment of the strut length, as will now be explained, permits independent selection of force capacities for each structural member.

In FIGS. 5 and 6 a modified form of the brace or strut is illustrated. The load frame is the same as that shown in 10, and corresponding parts are labeled with corresponding numbers. Biaxial loading (horizontal and vertical) is provided in the device of FIG. 5 as well, and as shown in FIG. 5, the upper platen 13 is raised and lowered relative to the lower or base platen 12 through the use of two hydraulic cylinders 15. The cylinders 15 provide a balanced load on the upper platen as it is moved along the upright columns 11.

The modified diagonal brace illustrated generally at 40 as shown comprises a lower sleeve or housing member 41, and a telescoping upper shaft or strut member 42. The lower member is pivotally mounted onto a pin 43 in a suitable manner to the base platen 12, and the strut or shaft member 42 is pivotally mounted with a pin 44 at its upper end to the upper platen 13. The member 42 telescopes into a provided receptacle indicated in dotted lines at 41A in the sleeve member 41. Rod 42 will telescope into the receptacle in a normal manner. The upper portions of the sleeve member 41 are split, as can be seen at 41B in FIG. 6, and this split permits clamping and releasing of the member 42 to either prevent or permit sliding movement of the member 42 relative to sleeve 41 and platen 12 by tightening the outer sleeve 41 down onto the strut member 42 through the use of a pair of hydraulic cylinders indicated at 45.

The cylinders 45 are constructed the same as the cylinders 31, and each has a piston 46 that actuates a rod 47 that as shown is threadably mounted into one section of the housing member 41, and is slidably mounted through other portions of the housing so that piston rod 47 spans the split or recess 41. When pressure is introduced into the interior of the cylinders 45 through a conduit connection 48, the pressure will act on the bottom side of the respective pistons 46 and will exert a force tending to clamp the housing 41 onto the strut or rod 42.

Two such cylinder assemblies 45 are utilized to insure secure clamping. The piston can be readily released from pressure to permit telescoping of rod 42 and sleeve 41 to in turn permit movement of the upper platen 13 when desired.

As shown in the dotted line position 44A of the upper end portion of the rod member 42, the rod and sleeve assembly will telescope a substantial distance to accommodate a wide variety of different positions of the platen.

The diagonal brace 40 can be utilized at all four sides of the load frame assembly, and also can be pivoted out of the way by removing either the pin 44 or the pin 43 and pivoting the brace on the other pin that is left in place to position clear of the space between the columns 11 to thereby permit insertion or removal of test apparatus.

In both forms of the invention a diagonal strut is provided which is releasably clamped relative to the platens to form a rigid load carrying member. In the first form of the invention the diagonal brace or strut could be releasably clamped at either end or at both ends. Also note that the members 25 and 30 slidably receive strut 21 and when clamped react loads between the strut and platens. The struts also could be pinned or otherwise held to prevent axial sliding movement relative to both platens.

What is claimed is:

1. In a load frame having a first platen and a second platen, at least one pair of spaced columns mounted on said first platen adjacent a side edge thereof, said second platen being mounted on said columns and being movable relative to said first platen to a desired position, means to support said second platen on said columns, and a diagonally extending strut means connected to both of said platens at locations on the respective platens displaced in lateral direction relative to the axes of the columns from mounting of the diagonal strut on the other platen, and means to releasably secure said strut means from movement relative to both platens.

2. The combination of claim 1 wherein said strut is pivotally mounted to one platen adjacent one of said columns, and is mounted to the other platen adjacent the other column in a pair of columns.

3. The combination as specified in claim 2, wherein said means to releasably secure includes means to clamp at least portions of said strut from sliding movement of said portions relative to one of the platens.

4. The combination of claim 1 wherein said means to releasably secure comprises hydraulic actuated clamp means to exert a clamping force on said strut means.

5. The combination of claim 1 wherein said means connecting one end of said strut means to one of said platens includes a member pivotally mounted relative to said one platen, said means to releasably secure clamping said strut means to prevent axial sliding movement of said strut means relative to the means pivotally mounted.

6. The combination as specified in claim 5 wherein said member comprises a disc like member rotatably mounted in a socket on said one platen.

7. The combination as specified in claim 6 wherein said strut slides relative to said disc member when the means to releasably clamp are released, said disc member and strut having mating grooved splines extending parallel to the longitudinal direction of said strut whereby additional friction force is provided through said mating spline members.

8. The combination of claim 5 wherein said member pivotally mounted comprises a sleeve slidably receiving said strut means.

9. The combination of claim 1 wherein said strut means comprises a strut having first and second telescoping portions, opposite ends of said strut means being pivotally connected to the respective platens, and said means to releasably secure comprising releasable clamp means adjacent the midportions of said strut means.

10. In combination with a load frame having a base platen, at least a pair of columns adjacent one side surface of said base platen, a second platen mounted on said columns and adjustably supported on said columns relative to said base platen, the improvement comprising a strut having a longitudinal axis, means to mount one end portion of the strut to one of said platens adjacent one of said columns, said strut extending diagonally and laterally toward the other of said platens adjacent the other column, means to guide said diagonal strut for axial sliding movement and to react loads between said strut and the other platen adjacent said other column, and means to clamp said strut against axial sliding movement relative to the means to guide and the other platen.

11. The combination of claim 10 wherein said platens are substantially the same size, and said strut is mounted on one lateral side and on the exterior of the platens.

12. The combination of claim 11 wherein said strut comprises two portions slidable relative to each other to permit the strut to be adjusted in length, said means to guide including one of said portions, opposite ends of said strut being pivotally mounted to the base and second platens, respectively, said means to clamp preventing sliding movement of the two portions when clamped.

* * * * *